United States Patent
Gregory

(10) Patent No.: US 8,052,930 B2
(45) Date of Patent: Nov. 8, 2011

(54) APPARATUS AND METHOD FOR EVALUATING EX VIVO TISSUE SAMPLES BY ELECTRICAL IMPEDANCE

(75) Inventor: William D. Gregory, Shorewood, WI (US)

(73) Assignee: WiSys Technology Foundation, Madison, WI (US)

( * ) Notice: Subject to any disclaimer, the term of this patent is extended or adjusted under 35 U.S.C. 154(b) by 446 days.

(21) Appl. No.: 12/417,075

(22) Filed: Apr. 2, 2009

(65) Prior Publication Data

US 2009/0253193 A1 Oct. 8, 2009

Related U.S. Application Data

(60) Provisional application No. 61/072,745, filed on Apr. 2, 2008.

(51) Int. Cl.
*G01N 21/00* (2006.01)

(52) U.S. Cl. .............. 422/82; 422/63; 422/64; 422/65; 422/67; 422/500; 422/501; 436/180

(58) Field of Classification Search .............. 422/63–65, 422/67, 82, 500–501; 436/180
See application file for complete search history.

(56) References Cited

U.S. PATENT DOCUMENTS

| | | |
|---|---|---|
| 4,263,551 A | 4/1981 | Gregory et al. |
| 4,493,039 A | 1/1985 | Gregory |
| 4,881,025 A | 11/1989 | Gregory |
| 6,522,910 B1 | 2/2003 | Gregory |
| 6,763,263 B2 | 7/2004 | Gregory et al. |

*Primary Examiner* — Jyoti Nagpaul
(74) *Attorney, Agent, or Firm* — Boyle Fredrickson, S.C.

(57) ABSTRACT

A device for characterizing ex vivo tissue employs a set of independent electrodes that may be used to scan the tissue by moving a voltage gradient across the tissue surface acquiring impedance spectrographs that may be mapped to an image.

16 Claims, 8 Drawing Sheets

APPARATUS AND METHOD FOR EVALUATING EX VIVO TISSUE SAMPLES BY ELECTRICAL IMPEDANCE

CROSS REFERENCE TO RELATED APPLICATION

This application claims the benefit of U.S. provisional application 61/072,745 filed Apr. 2, 2008 and hereby incorporated by reference.

BACKGROUND OF THE INVENTION

The present invention relates generally to instruments for evaluating tissue samples in medical pathology, and in particular to a device that characterizes tissue samples using precise measurements of electrical impedance of the tissue.

The diagnosis of cancer and other diseases is often made by the examination of tissue samples removed from the patient during a biopsy or surgical procedure. The tissue sample may be preserved chemically and then stained and sliced into layers that are on an order of one to several cells in thicknesses. These sections are examined by a pathologist who may study these sections under a microscope to reach a conclusion about whether the tissue is cancerous.

The above process may take substantial time to complete and therefore an alternate procedure called a ""frozen section"" may be used that eliminates the step of chemical preservation and encases the specimen in plastic and freezes the specimen. This process can be accomplished in less than an hour, but requires considerable skill. Further the resulting sections provide lower resolution images, and therefore must often be followed by a conventional chemical preservation process described above.

In both of these techniques, only small sections of tissue may be analyzed and accordingly many adjacent sections must often be studied to definitively diagnose the disease in an organ.

SUMMARY OF THE INVENTION

The present invention provides a system that can rapidly assess the electrical impedance spectrum (complex impedance as a function of frequency) of thin but large area tissue samples without sectioning or other preparation. There is currently evidence that impedance characteristics of tissue may provide a method of rapidly distinguishing benign from cancerous tumors.

Specifically, the present invention provides an apparatus for tissue sample analysis having a first electrode array providing a surface for receiving an ex vivo tissue sample in abutment with the surface, the surface providing a plurality of electrically independent voltage measurement points and voltage application points. An electronic computer communicates with the first electrode array to control voltage applied to the voltage application points and to read voltages obtained at the voltage measurement points. This electronic computer operates according to a stored program to: (a) establish a voltage gradient among the voltage application points defining a boundary across the first electrode array; (b) sweep the boundary across the first electrode array while the first electrode array is in contact with the tissue sample; (c) monitor the voltage measurement points at the boundary to measure impedance at multiple points along the boundary for each of multiple different locations of the boundary during the sweep; and (d) provide an output characterizing the tissue sample according to the measured impedance at the multiple points.

It is thus a feature of at least one embodiment of the invention to provide an accurate method of quickly characterizing relatively large tissue samples over multiple points. By sweeping a voltage gradient across the tissue sample, multiple impedance points can be measured without errors caused by field fringing.

The voltage gradient may define sequential first and second boundaries that are mutually substantially perpendicular and the operation of sweeping the boundary across the first electrode array may sweep the first and second boundaries along substantially perpendicular axes. The operation of monitoring the voltage at the measurement points may be repeated for each of the boundaries to measure impedance at each of the multiple points twice, once during a sweep of the first and second boundaries.

It is thus a feature of at least one embodiment of the invention to provide multiple measurements and to provide a measurement system that accommodates tissue anisotropy.

At least one of the current and voltage at the voltage application points may substantially define a step function over an area of the first electrode array.

It is thus a feature of at least one embodiment of the invention to provide a gradient producing a well-characterized current flow through the tissue.

The electronic computer may control the voltage applied to the voltage application points to provide a predetermined current through the tissue.

It is thus a feature of at least one embodiment of the invention to provide a measurement mode eliminating the need for correction of the measured voltage drops by current flow.

Alternatively, the electronic computer may control the voltage applied to the voltage application points independent of the current through the tissue and monitor the current at the voltage application points to measure impedance at the multiple points along the boundary.

It is thus a feature of at least one embodiment of the invention to provide a measurement mode allowing simplified application of voltages to the electrodes.

The voltage application points and voltage measurement points are electrodes having a surface treated to reduce electrode polarization.

It is thus a feature of at least one embodiment of the invention to improve the precision of the impedance measurement by reducing electrode polarization effects caused by ion conduction in the tissue.

The voltage application points and voltage measurement points are electrodes having a surface adapted not to pierce the tissue.

It is thus a feature of at least one embodiment of the invention to provide a measurement technique that does not unduly damage the tissue.

The apparatus may also provide a second electrode array like the first electrode array and positionable opposite the first electrode array to sandwich the tissue sample therebetween in contact with the voltage measurement points and voltage application points of the first and second electrode arrays. In this case, the electronic computer also communicates with the second electrode array to provide a spatially corresponding gradient on the second electrode array, to monitor the measurement points at a boundary on the second electrode array to measure impedance at multiple points along the boundary for each of multiple different locations of the boundary during the sweep, and to provide an output characterizing the tissue"

sample according to the measured impedance at the multiple points on both the first and second electrode array.

It is thus a feature of at least one embodiment of the invention to better characterize the impedance through the entire thickness of thin slices of tissue.

The gradient boundary may be substantially a line.

It is thus a feature of at least one embodiment of the invention to provide a simplified electrode layout and data collection method that reduces current field fringing and distortion.

The first and second electrode arrays may be positionable at less than 1 cm separation.

It is thus a feature of at least one embodiment of the invention to provide direct measurement of tissue samples without freezing and sectioning.

The output may be an image mapping impedance to spatial locations corresponding to the voltage measurement points.

It is thus a feature of at least one embodiment of the invention to provide an assessment of tissue samples in which cancer cells, for example, may comprise only a portion. The imaging capability allows comprehensive analysis of larger tissue samples.

The output may provide a numeric index characterizing the tissue.

It is thus a feature of at least one embodiment of the invention to provide a simple metric characterizing tissue.

The electrode array may provide electrodes that are selectively switched by the computer between voltage application points and voltage measurement points, and the electronic computer controls the voltage application points and voltage measurement points so that a pair of voltage measurement points are separated by the boundary and are flanked by voltage application points. Alternatively, the electrode array may provide electrodes that may be simultaneously voltage application points and voltage measurement points.

It is thus a feature of at least one embodiment of the invention to permit either four-lead or two-lead type resistance measurements.

The electronic computer may first measure impedance by controlling the voltage application points and voltage measurement points so that a pair of voltage measurement points are separated by the boundary and are flanked by voltage application points in a four-lead impedance measurement, and may second measure impedance by controlling the voltage application points and voltage measurement points to be combined in a two-lead impedance measurement. The electronic computer may in this case evaluate the difference between the four-lead and two-lead impedance measurements to deduce electrode polarization.

It is thus a feature of at least one embodiment of the invention to provide a method of characterizing the effects of electrical polarization to correct the output characterizing the tissue sample or provide a warning to the user if polarization effects are substantial.

These particular features and advantages may apply to only some embodiments falling within the claims and thus do not define the scope of the invention.

DETAILED DESCRIPTION OF THE PREFERRED EMBODIMENT

Figure 1:
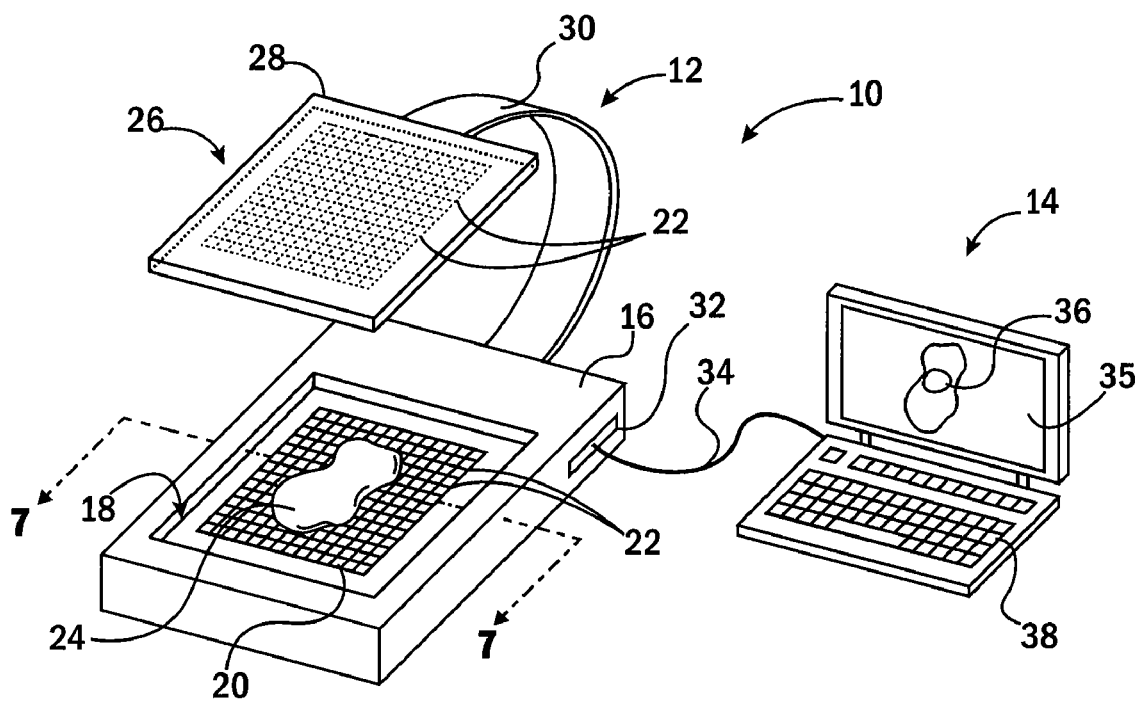
FIG. 1 is a perspective view of an impedance measuring device according to the present invention having an electrode array connected to a laptop computer or the like, the elements together providing tissue analysis.

Referring now to FIG. 1, the impedance measuring apparatus 10 of the present invention may employ a tissue sample unit 12 and associated computer 14, the latter providing display and program input capabilities as will be described below. In alternative embodiments, it will be understood that the computer 14 functions may be incorporated into the tissue sample unit 12.

In the embodiment shown, the tissue sample unit 12 includes a base portion 16 having a well 81 exposing at its bottom a first planar electrode array 20 comprised of perpendicular and rectilinear rows and columns of electrodes 22 electrically isolated from each other by intervening channels. The well 18 is sized to receive an unprocessed tissue sample 24 typically several millimeters thick and no more than 1 cm thick (measured perpendicularly to the surface of the array 20) and having a height and width (measured along the surface of the array 20) of less than approximately 4 cm. The electrode array 20 is sized so that the tissue sample 24 may lie within the boundaries described by the limits of the electrodes 22, thus contacting the electrodes 22 over its entire surface.

A second electrode array 26 may be positioned on a carrier 28 fitting within the well 18 so that an interface between the walls of the carrier 28 and walls of the well 18 serve to align the second electrode array 26 with the first electrode array 20 such that each electrode 22 of the first and second electrode arrays 20 and 26 are aligned in opposition about the tissue sample 24. In this configuration, the electrode array 20 contacts an underside of the tissue sample 24 and the electrode array 26 contacts the top of the tissue sample 24 to sandwich the tissue sample 24 there between.

A flexible conductor 30 may communicate between the electrode array 26 and the base portion 16 so that electrical signals associate with all the electrodes 22 can be brought together within the base portion 16.

Electrical signals to and from each electrode 22 are processed by multiplexer/demultiplexer circuitry within the base portion 16 as will be described and may be conveyed through a connector 32 on the base portion 16 via a cable 34 such as a USB cable to computer 14. The computer 14 may include a display 35 displaying an image 36 of the tissue sample 24 as will be described and may provide for an input device 38 such as a keyboard for inputting data.

Figure 2:
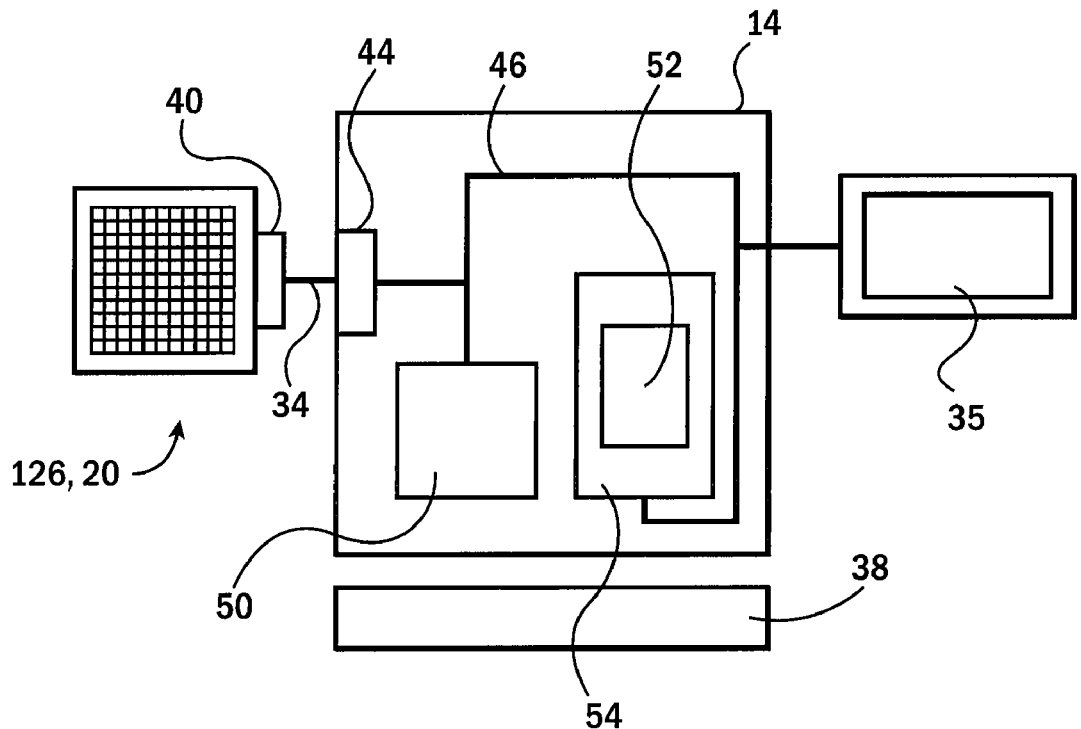
FIG. 2 is a block diagram of the invention of FIG. 1 showing the components of the electrode array and the associated computer which may also be incorporated into one housing.

Referring now to FIG. 2, a USB interface circuit 40 in the sample unit 12 connects via the USB cable 34 with interface circuit 44 in the computer 14. The interface circuit 44 may in turn attach to an internal computer bus 46 also communicating with the display 35 and input device 38 as well as an internal microprocessor 50 executing a stored program 52 contained in a memory 54. In one embodiment, as described above, the components of the sample unit 12, the interface circuits 40 and 44, the microprocessor 50, and the memory 54 may all be contained in a common housing 55.

Figure 3:
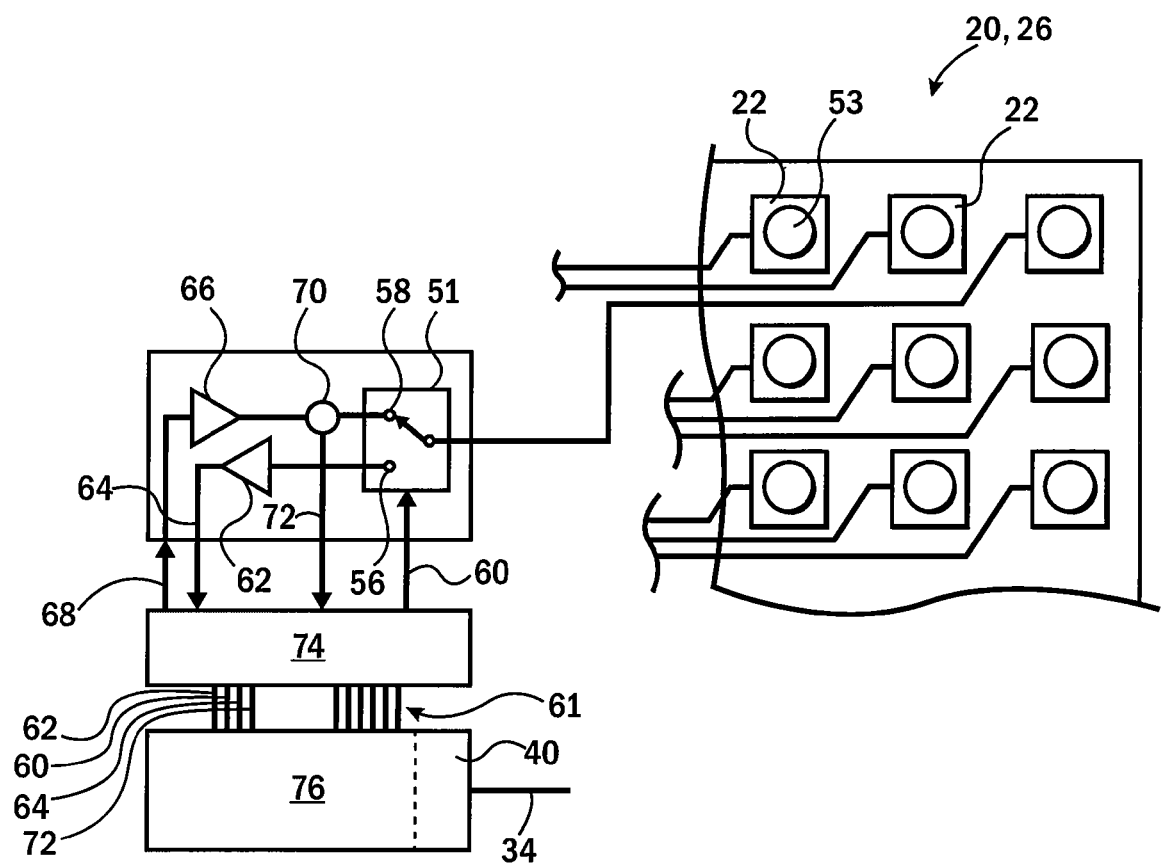
FIG. 3 is a fragmentary schematic diagram showing electrical interconnection of multiple electrodes of the electrode array to voltage measurement and voltage application points using a multiplexer/demultiplexer.

Referring now to FIG. 3, as mentioned, each of the electrode arrays 20 and 26 provides a set of electrodes 22. These electrodes 22 provide an outer surface facing the tissue sample 24 having a raised tissue-contacting portion 53 increasing the contact area between the electrode 22 and the tissue sample 24. The surface of the electrodes 22 contacting the tissue sample 24 may be treated to reduce electrical polarization, for example, with a silver/silver chloride coating of the type used in ECG electrodes or a platinum black application according to techniques well known in the art. These coatings serve to reduce spurious voltage measurements caused by the accumulation at the electrodes of charged ions such as form a principal conduction path within the tissue.

Each electrode 22 may be electrically connected to a solid-state single-pole, double-throw switch 51 that may in turn connect the electrode 22 alternately to a voltage measurement point 56 or to a voltage application point 58 under the control of an electrical switching signal 60. The voltage measurement point 56 may connect to an input of high impedance amplifier 62 to produce a measurement signal 64. The voltage application point 58 connects to the output of a buffer amplifier/sample and hold circuit 66 receiving a voltage command 68. The output of the buffer amplifier/sample and hold circuit 66 passes through a current sensor 70 measuring the current flowing into or out of the voltage application point 58 to produce a current signal 72.

The elements 51, 62, 66, and 70 are duplicated for each of the electrodes 22 and exchange respective signals 60, 64, 68, and 72 with a microcontroller 76 via an analog multiplexer/demultiplexer 74, which switches among the electrodes 22 according to address signal 61 generated by the microcontroller 76 so that one electrode 22 may be written to or read. The microcontroller 76 may implement the USB interface 40 providing communication to the computer 14 through cable 34.

Figure 5A:
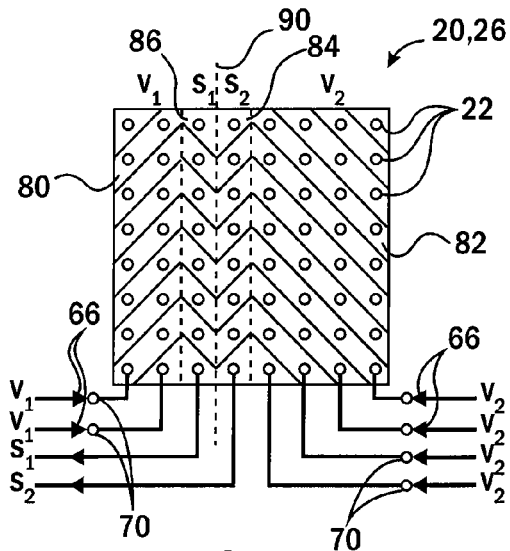
FIGS. 5a-d are top plan views of one electrode array of the impedance measuring device as operated according to the program of FIG. 4 showing voltage zones generating a scanned measurement boundary across the electrode array and hence across the tissue sample proximate to the electrode array.

Referring now to FIG. 5a, the computer 14 and tissue sample unit 12 operating in tandem, control the electrodes 22 to impose different voltage patterns thereacross. For example, during a columns scan, electrodes 22 in a first set of columns forming a zone 80 may connect to a first voltage V1 (the first two columns on the right as depicted) and the electrodes 22 in a second set of columns forming a zone 82 may connect to a second voltage V2 different from the first voltage (the last four columns on the left as depicted). This voltage pattern creates a voltage difference across two center columns 84 and 86 between the zone 80 and zone 82 which provides sensing columns S1 and S2 flanking a column-aligned boundary 90.

Figure 5B:
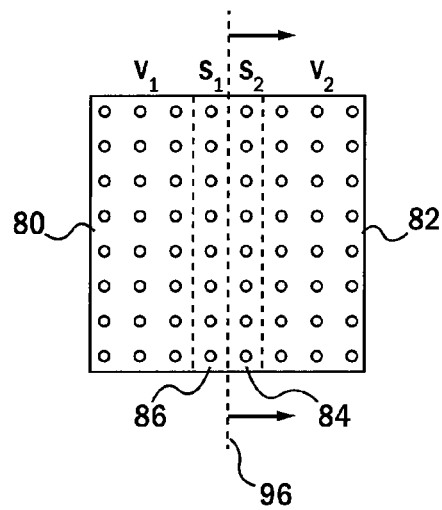

By manipulating the signals 60 and 68, the boundary 90 may be moved from left to right (as shown in FIG. 5b). In a complete four-lead columns scan, the boundary 90 can start as far over as the interface between the second and third columns from the left and move to the interface between second and third column from the right being positioned momentarily in between each column At each position of the boundary 90, a voltage difference may be measured across the boundary 90 by electrodes 22 of sensing columns S1 and S2 being the mathematical difference between the voltage measured at an electrode 22 in sensing column Si and an electrode 22 in the same row in sensing column S2.

For each pair of electrodes 22 and computed voltage drop, a corresponding measurement of current is obtained and an impedance value deduced at the intersection between that row and the boundary 90. As the boundary 90 moves from left to right, impedance measurements may be made at multiple row and boundary locations over the two-dimensional surface of the arrays 20 and 26.

Figure 6:
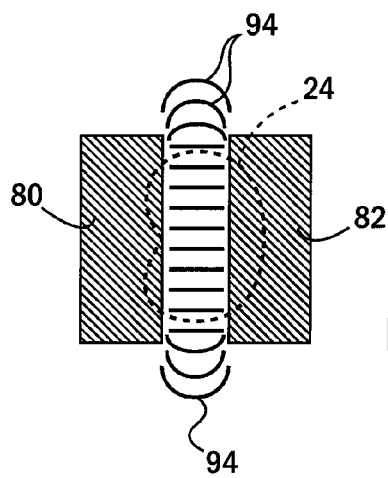
FIG. 6 is a top plan view similar to FIGS. 5 showing fringing current fields avoided by the present scanning system within tissue sample.

Referring momentarily to FIG. 6, current passing between electrodes 22 on either side of the boundary 90 within the sensor zones S1 and S2 may with reasonable precision be considered equal to the current passing through the tissue sample 24 in a line between those electrodes because the voltage pattern of electrodes in the zones 80 and 82 provide essentially planar opposed electrical fields, this geometry eliminating fringing current flow 94 except at the very edge rows removed from the tissue sample 24. By keeping the tissue sample 24 smaller than the size of the array 20, the approximation of linear current flow between electrodes 22 is good throughout the entire tissue sample 24 and therefore current in the tissue between each electrode pair can be approximated by the average of the current measured flowing out of and into the electrodes 22 of that pair.

Figure 5C:
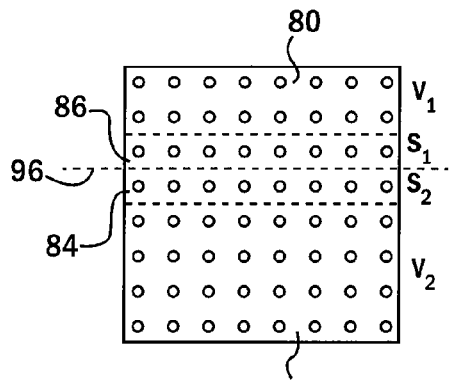
Figure 5D:
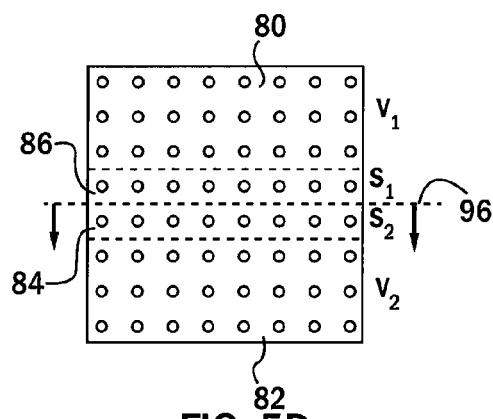

Referring now to FIGS. 5c and 5d, the process of scanning the boundary 90 may be repeated with a new boundary 96 oriented horizontally and thus parallel to the rows. In this case, the voltages of V1 and V2 cover contiguous blocks of rows on either side of horizontally oriented sensor regions S1 and S2 as shown in FIG. 5b. The boundary 96 may be scanned from top to bottom of the arrays to obtain impedance measurements at pairs of vertically flanking electrodes 22 for each of the columns. Impedance values obtained during this scan maybe recorded separately or combined with the values contained during the horizontal scan.

While the preferred embodiment uses a boundary 96 that is substantially linear extending across the electrode array 20, it will be understood that variations on this are possible including, for example, a boundary that encloses a small surface on the electrode array and that is scanned, for example, in a raster pattern. Such a boundary would not provide the benefits of eliminating the effects of fringing fields as will be described but could be useful in exploring other aspects of the impedance at the surface.

Figure 7:
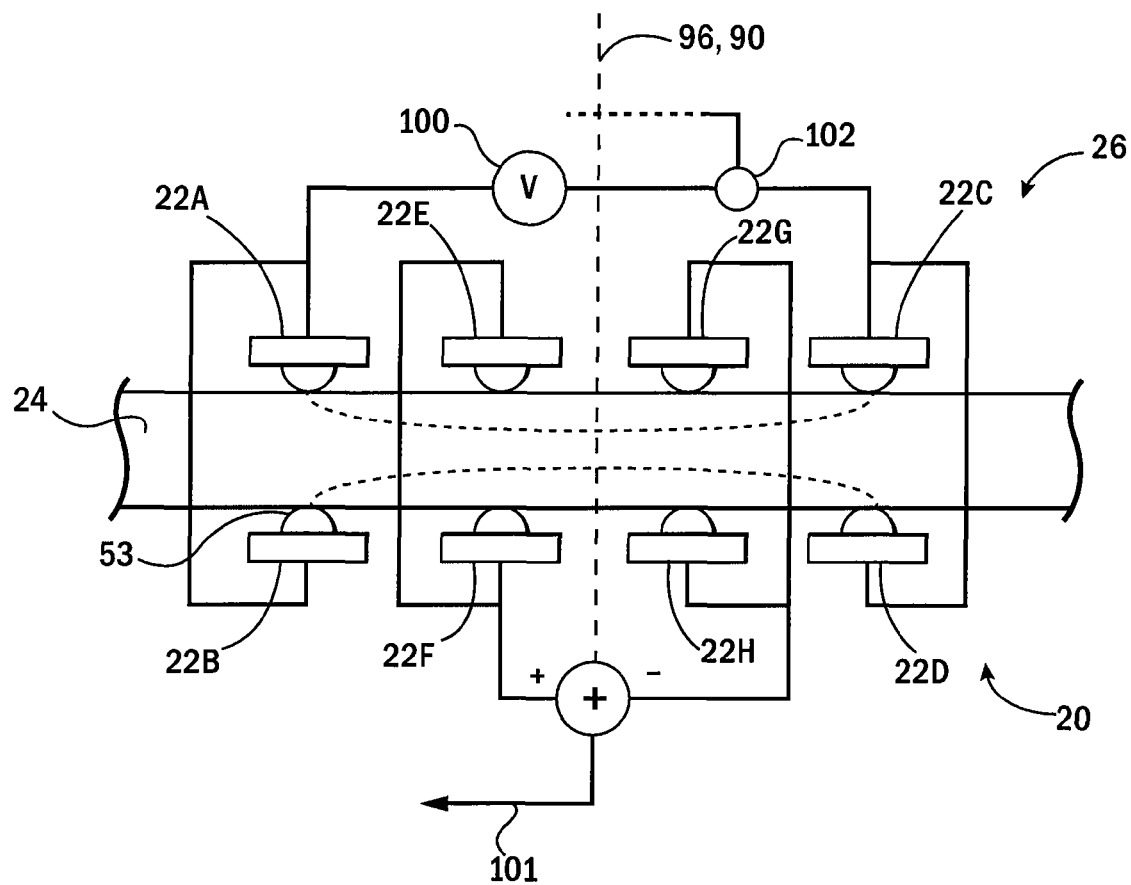
FIG. 7 is a fragmentary cross-sectional view taken along line 7-7 of FIG. 1 showing electrical connections for a four-lead impedance measurement using scanning pattern of FIG. 5.

Referring now to FIG. 7, the above measurements may occur simultaneously on the upper electrode array 26 and the lower electrode array 20. Thus, driving electrodes 22a and 22b on opposite sides of the tissue sample 24 on one side of the boundary 90 (or 96) removed from the boundary 90 (or 96) by sensing electrodes 22e and 22f may be given the same electrical potential (V1), and electrodes 22c and 22d on opposite sides of the tissue sample 24 and symmetrically offset from the electrodes 22a and 22b about the boundary 90 (or 96) may be given the second electrical potential (V2) to establish a virtual voltage source 100 therebetween implemented by a combination of buffer amplifier/sample and hold circuits 66. Current between the electrodes 22a and 22b and electrodes 22c and 22d may be measured as indicated by virtual current sensor 102 implemented by a combination of current sensors 70.

Voltages measured at electrodes 22e and 22f on one side of the boundary 90 (or 96) may be averaged and subtracted from voltages measured at electrodes 22g and 22h on the other side of the boundary 90 (or 96) to produce a voltage difference or voltage drop 101 across the boundary 90 (or 96). The voltage drop together with the current measured at virtual current sensor 102 yields an impedance measurement. For thin tissue samples 24, the electrodes 22 on both sides of the tissue sample 24 promote a uniformity of current flow and a measurement that is sensitive to impedance throughout the thickness of the tissue sample 24.

Figure 8:
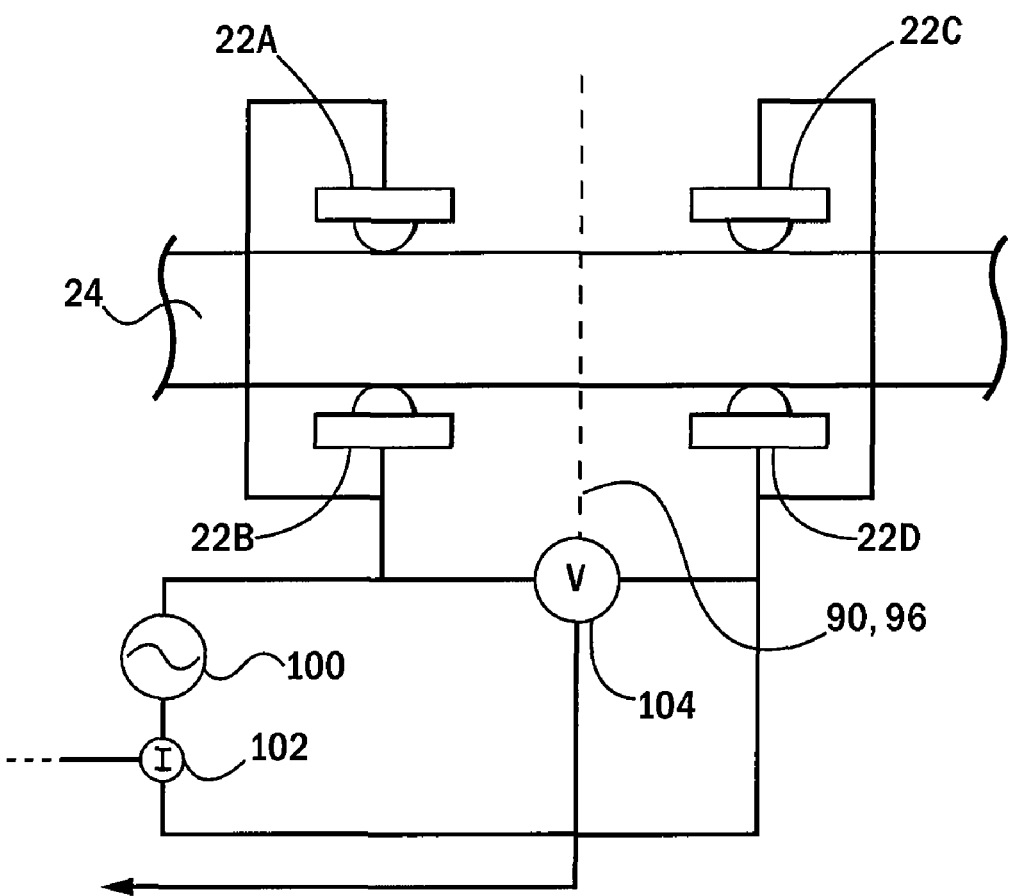
FIG. 8 is a figure similar to that of FIG. 7 showing a two-lead measurement.

Referring now to FIG. 8, the above description has been that of a four-lead measurement. The present invention may also operate in the two-lead mode that may be useful for measuring impedances at the edges of the arrays 20 and 26 wherefore contiguous electrodes are not readily obtained, or in other modes, for example between electrodes of the arrays 20 and 26. As will described further below, the two-lead mode may also be used to provide an estimation of electrical potential artifacts occurring in the measurement of currents through tissue to improve the accuracy of the impedance measurement. In the two-lead measurement mode, only four electrodes 22a-22d are needed for an impedance measurement in contrast to the eight electrodes 22a-22h shown in FIG. 7.

As shown in FIG. 8, in a two-lead measurement scan electrodes 22a and 22b are positioned on opposite sides of the tissue sample 24 on one side of the boundary 90 (or 96) which is scanned horizontally and vertically as described above. The electrodes 22a and 22b may be connected to a first potential V1 provided by virtual voltage source 100. Similarly, electrodes 22c and 22d on opposite sides of the tissue sample 244 and on the other side of the boundary 90 (or 96) may be connected to the second potential V2 of voltage source 100 with the current therebetween being measured by virtual current sensor 102.

The voltage difference between the pair of electrodes 22a, 22b and the pair of electrodes 22c, 22d, may be measured directly by a virtual voltmeter 104 implemented by a measurement of the signals 68 driving the corresponding buffer amplifier/sample and hold circuits 66. The impedance may be then calculated as the ratio of the voltage of virtual voltmeter 104 to the current measured by virtual current sensor 102.

Figure 9:
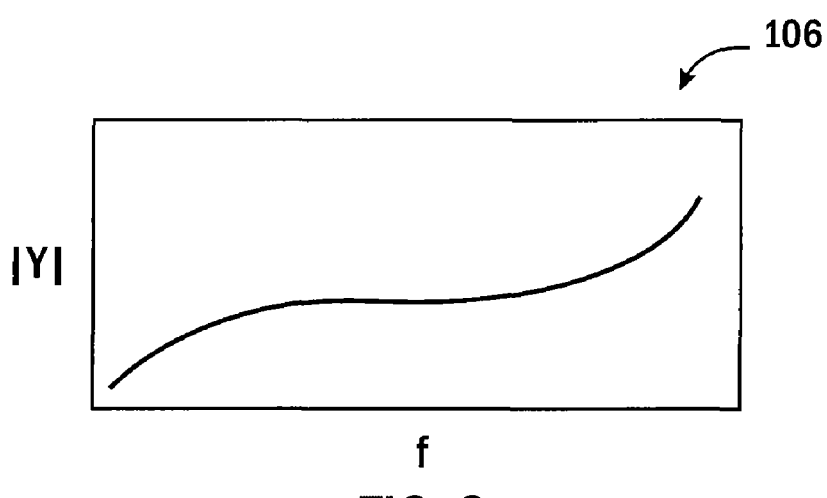
FIG. 9 is a sample impedance spectrogram produced by the present invention.

In the preferred embodiment, the invention measures complex impedance using voltages V1 and V2 that create alternating currents through the tissue sample 24 over a range of frequencies from 10 Hz to 1 MHz. The complex impedance at each frequency creates an impedance spectrum 106 as shown in FIG. 9 indicating, for example, the magnitude of the impedance as a function of frequency or the real and imaginary parts of the impedance (not shown) or phase angle as a function of frequency to yield a complete understanding of the impedance of the tissue.

Figure 10:
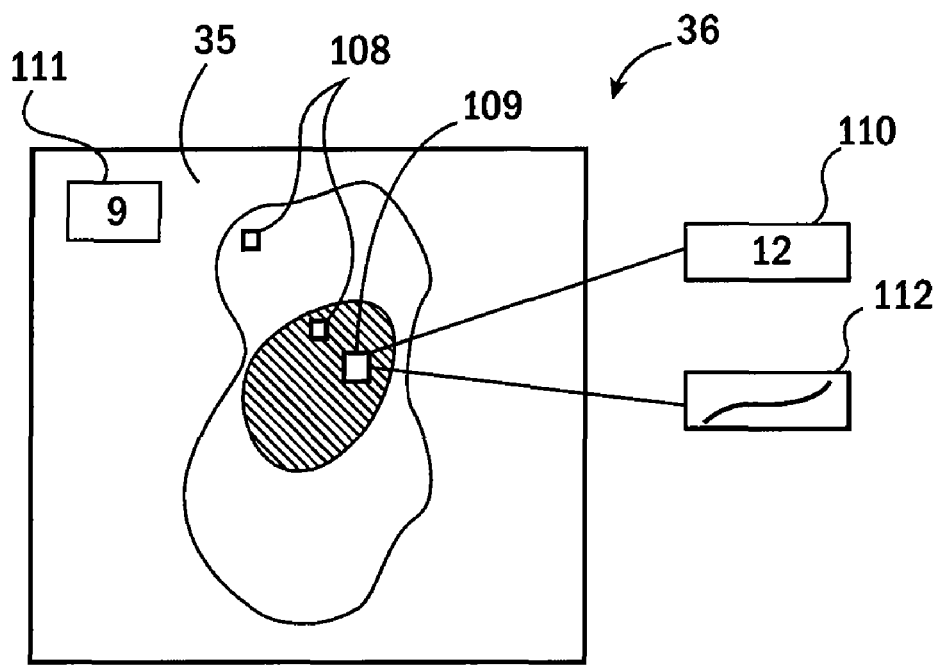
FIG. 10 is an example output display produced by the present invention providing an image of the tissue impedance together with quantitative and spectrographic data localized to a cursor location in the image.

Referring to FIG. 10, the data of each impedance spectrum 106 may be mapped to pixels 108 of an image 36 having a location corresponding to the measurement points of the impedance. Particular values or classifications of the impedance spectrum 106 may be used to determine the color or grayscale of the pixels 108. Alternatively, a frequency peak or local maxima in the spectrum 106 may be mapped to a particular color of the pixels 108 to yield a color image having a qualitative representation of the changes in the tissue sample over its area in the area of the arrays 20 and 26. Optionally the user may manipulate a cursor 109 over the image 36 linked to windows 110 and 112 providing respectively a numeric value reflecting one or more important parameter of the frequency spectrum 106 and the frequency spectrum 106 itself. General statistical metrics, for example a likelihood of the tissue being cancerous or percentages of cancerous tissue, may be presented in a window 111. Analysis of impedance spectrums is described in "Correction Of Electrode Polarization Contributions to the Dielectric Properties of Normal and Cancerous Breast Tissues at Audio/Radiofrequencies" Stoneman, M. R. et al. Phys. Med. Biol. 52 (2007) 6589-6604, hereby incorporated by reference.

Figure 11:
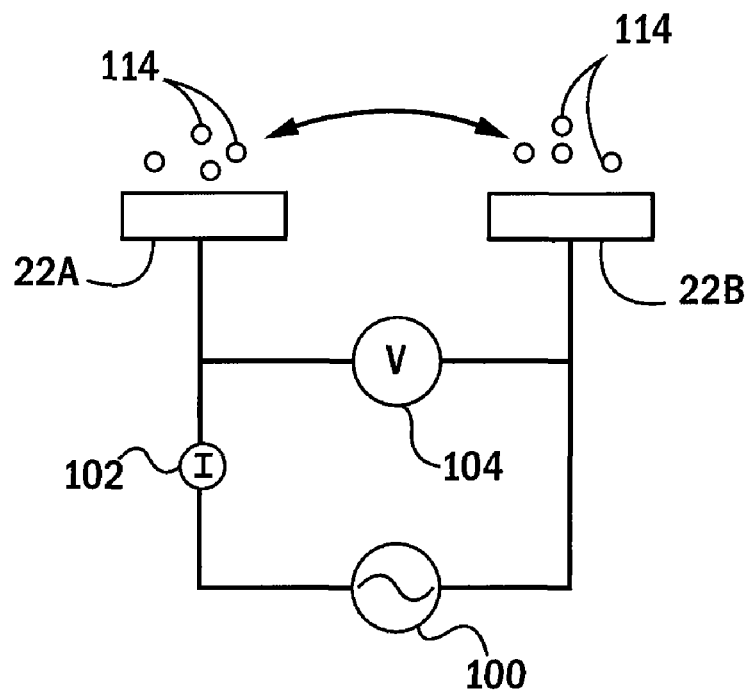
FIG. 11 is a simplified representation of electrical polarization effects occurring in a two-lead measurement.

Referring now to FIG. 11, the present invention contemplates that multiple scans of the tissue sample 24 may be completed, first in a two-lead mode as described with respect to FIG. 8, and second in a four-lead mode as described with respect to FIG. 7. As shown in FIG. 11, the two-lead mode has the problem of being sensitive to lead impedance and contact resistance because of the necessity of current flow through electrodes 22a and 22b which also serve simultaneously as the measurement points. In addition, to the extent that the conduction of electricity in the tissue sample 24 is by means of ions 114, electrical potentials may build up at the electrodes 22a or 22b corrupting the measurement of voltage drop thus adversely affecting the impedance measurement.

Figure 12:
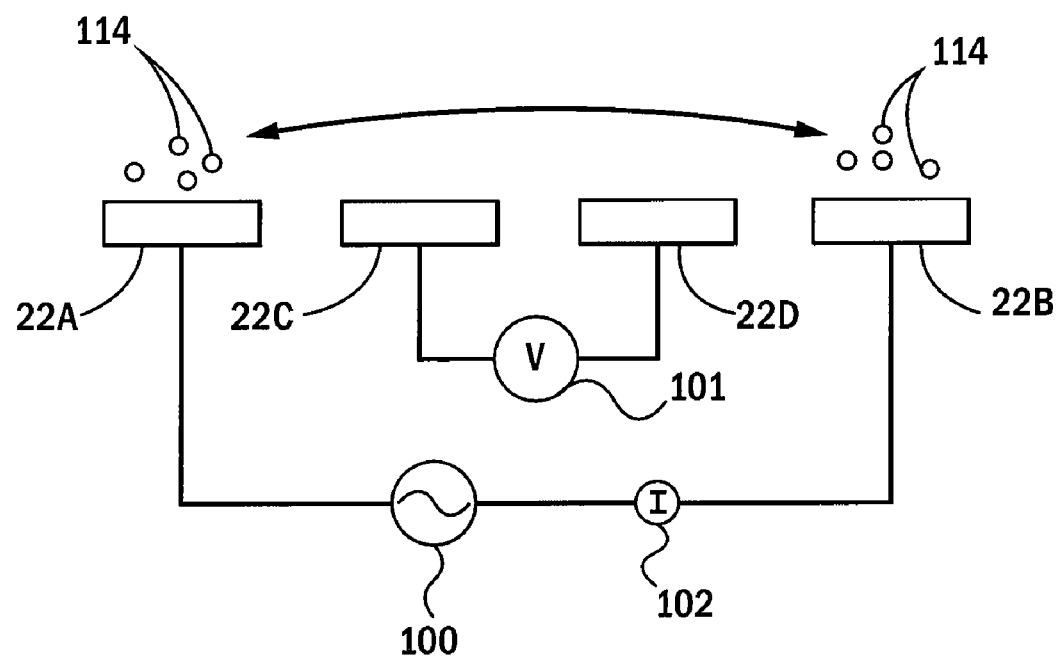
FIG. 12 is a figure similar to that of FIG. 11 showing a reduction in electrical polarization effects in a four-lead measurement.

In contrast, as shown in FIG. 12, in the four-lead mode, electrodes 22a and 22b used for voltage application can be separated from electrodes 22c and 22d used for a measurement of voltage drop. This measurement of voltage at electrodes 22c and 22d can be conducted with very little current flow (eliminating the effect of the impedance or contact resistance). Similarly, this reduced current flow at electrodes 22c and 22d eliminates or reduces problems caused by the accumulation of ions 114. The present invention contemplates that both of these measurements may be used and the difference between the measurements in areas where both measurements are made may be used to provide a calibration factor indicating offset caused by electrical potential that can be used to correct the impedance measurements, for example, using the two-lead mode, near the edges of the arrays 20 and 26.

Figure 4:
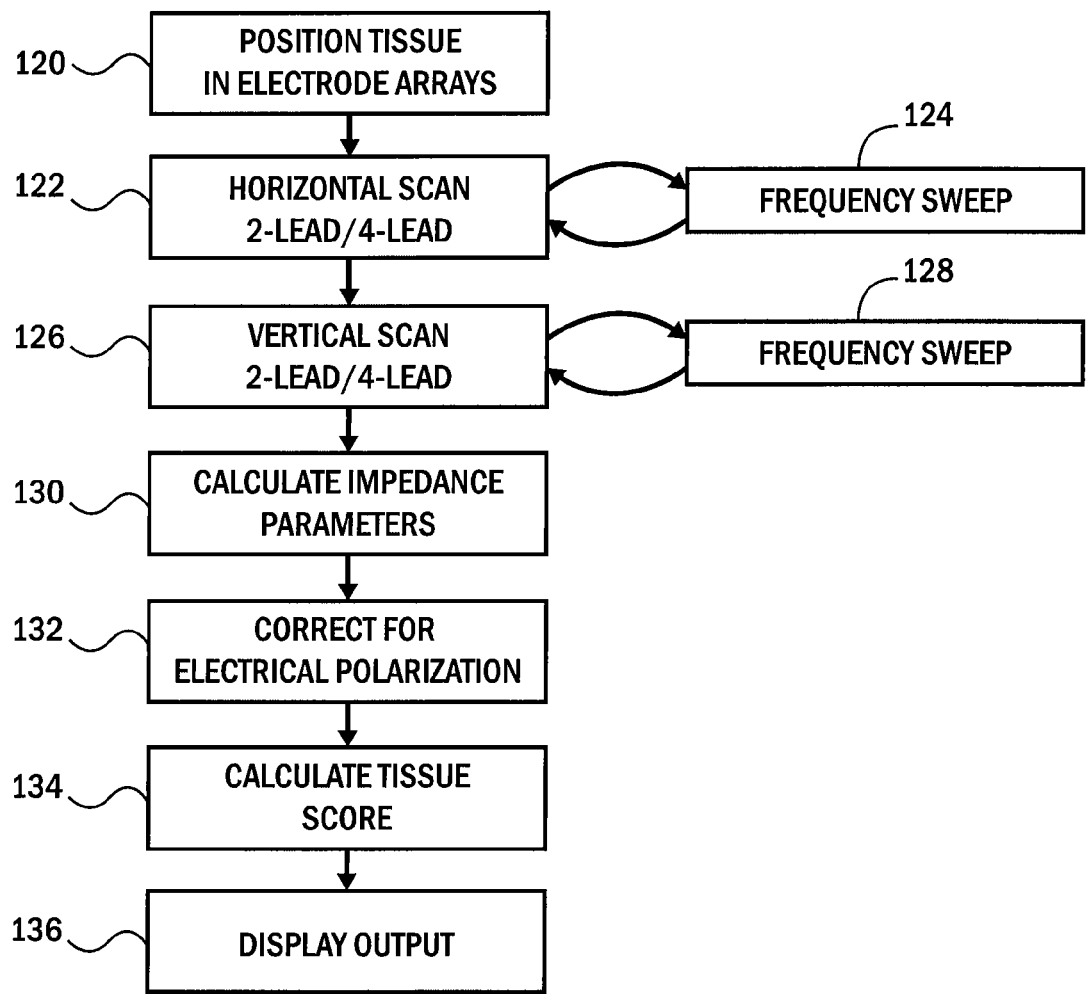
FIG. 4 is a flow chart of the program executed by the computer of FIGS. 1, 2, and 3 for providing impedance scans.

Referring now to FIG. 4, in operation then, the present invention may begin by the placement of tissue sample 24 in the tissue sample unit 12 as shown in FIG. 1 sandwiched between upper array 26 and lower array 20 as indicated by process block 120. A horizontal scan may be conducted per process block 122 as shown in FIGS. 5a and 5b using the two-lead and four-lead modes. At each different scan location (defined by the position of the boundary 90), as indicated by process block 124, a set of impedance measurements may be made at each row for a range of different frequencies to establish spectrum 106 for each row at the particular boundary location.

At succeeding block 126 and 128, a vertical scan may be conducted and frequency measurements made in a manner analogous to process blocks 122 and 124.

At process block 130, the program may collect the measured information of current and voltage obtained during the scans and calculate impedance parameters at points centered between each pair of sensing electrodes. Each of these impedance parameters may be in the form of a spectrum and associated with a particular coordinate on the arrays 20 and 26.

The collected impedance data for corresponding points taken in different scan directions may be combined, for example by averaging, and the impedance measurements over the arrays may be further processed, for example, by spatial filtering or the like.

Optionally, at process block 132 the impedance measurements of process block 130 may be corrected by compensating the two-lead measurements contributing to the calculation of impedance for electrical polarization deduced as described above.

At process block 134 tissue scores may be calculated reducing the data to simple scales or dimensions, for example, an arbitrary scale from 1 to 10 indicating a likelihood of cancer or the percentage of the measurements indicating a likelihood of cancer.

Finally, at process block 136 an output such as shown in FIGS. 9 or 10 may be provided.

The present invention has been described in terms of the preferred embodiment, and it is recognized that equivalents, alternatives, and modifications, aside from those expressly stated, are possible and within the scope of the appending claims.

I claim:

1. An apparatus for tissue sample analysis comprising:
   a first electrode array providing a surface for receiving an ex vivo tissue sample in abutment with the surface, the surface providing a plurality of electrically independent voltage measurement points and voltage application points;
   an electronic computer communicating with the first electrode array to control voltage applied to the voltage application points and to read voltages obtained at the voltage measurement points, the electronic computer programmed to analyze tissue sample by
   (a) establishing a voltage gradient among the voltage application points defining a boundary across the first electrode array;
   (b) sweeping the boundary across the first electrode array while the first electrode array is in contact with the tissue sample;
   (c) monitoring the voltage measurement points at the boundary to measure impedance at multiple points along the boundary for each of multiple different locations of the boundary during the sweep; and
   (d) providing an output characterizing the tissue sample according to the measured impedance at the multiple points.

2. The apparatus of claim 1 wherein the operation of establishing the voltage gradient defines sequential first and second boundaries that are mutually substantially perpendicular and wherein the operation of sweeping the boundary across the first electrode array sweeps the first and second boundaries along substantially perpendicular axes whereby the operation of monitoring the voltage at the measurement points is repeated for each of the boundaries to measure impedance at each of the multiple points twice, once during a sweep of the first and second boundaries.

3. The apparatus of claim 1 wherein at least one of a current and voltage at the voltage application points substantially defines a step function over an area of the first electrode array.

4. The apparatus of claim 1 wherein the electronic computer controls the voltage applied to the voltage application points to provide a predetermined current through the tissue.

5. The apparatus of claim 1 wherein the electronic computer controls the voltage applied to the voltage application points independent of a current through the tissue and wherein the electronic computer further operates to monitor the current at the voltage application points to measure impedance at the multiple points along the boundary.

6. The apparatus of claim 1 wherein the voltage application points and voltage measurement points are electrodes having a surface treated to reduce electrode polarization.

7. The apparatus of claim 1 wherein the voltage application points and voltage measurement points are electrodes having a surface adapted not to pierce the tissue.

8. The apparatus of claim 1 further including a second electrode array providing a surface providing a plurality of electrically independent voltage measurement points and voltage application points, the second electrode array positionable opposite the first electrode array to sandwich the tissue sample therebetween in contact with the voltage measurement points and voltage application points of the first and second electrode arrays; and
   wherein the electronic computer also communicates with the second electrode array to provide a spatially corresponding gradient on the second electrode array and to monitor the measurement points at a boundary on the second electrode array to measure impedance at multiple points along the boundary for each of multiple different locations of the boundary during the sweep and to provide an output characterizing the tissue sample according to the measured impedance at the multiple points on both the first and second electrode array.

9. The apparatus of claim 1 wherein the boundary is substantially a line.

10. The apparatus of claim 1 wherein the first and second electrode arrays are positionable at less than 1 cm separation.

11. The apparatus of claim 1 wherein the output provides an image mapping impedance to spatial locations corresponding to the voltage measurement points.

12. The apparatus of claim 1 wherein the output provides a numeric index characterizing the tissue.

13. The apparatus of claim 1 wherein the electrode array provides electrodes that may be selectively switched by the computer between voltage application points and voltage measurement points and the electronic computer controls the voltage application points and voltage measurement points so that a pair of voltage measurement points are separated by the boundary and are flanked by voltage application points.

14. The apparatus of claim 1 wherein the electrode array provides electrodes that may be simultaneously voltage application points and voltage measurement points.

15. The apparatus of claim 1 wherein the electrode array provides electrodes that may be selectively switched by the computer between:
   (1) either voltage application points and voltage measurement points for four-lead impedance measurement and
   (2) both voltage application points and voltage measurement points for two-lead impedance measurement; and
   wherein the electronic computer:
   (1) first measures impedance by controlling the voltage application points and voltage measurement points so that a pair of voltage measurement points are separated by the boundary and are flanked by voltage application points in a four-lead impedance measurement, and
   (2) second measures impedance by controlling the voltage application points and voltage measurement points to be combined in a two-lead impedance measurement;
   wherein the electronic computer evaluates a difference between the four-lead and two-lead impedance measurements to deduce electrode polarization.

16. The apparatus of claim 15 wherein the deduced electrode polarization is used to correct the output characterizing the tissue sample.

* * * * *